United States Patent [19]
Arraudeau et al.

[11] Patent Number: 5,035,885
[45] Date of Patent: Jul. 30, 1991

[54] NONCOMPACTED MAKE-UP POWDER OR POWDER FOR THE CARE OF THE BODY AND FACE CONTAINING SYNTHETIC THERMOPLASTIC MATERIAL IN THE FORM OF HOLLOW MICROSPHERES

[75] Inventors: Jean-Pierre Arraudeau, Paris; Anne Boelle, Meudon, both of France

[73] Assignee: L'Oreal, Paris, France

[21] Appl. No.: 329,880

[22] Filed: Mar. 28, 1989

Related U.S. Application Data

[63] Continuation-in-part of Ser. No. 66,165, Jun. 25, 1987, abandoned.

[30] Foreign Application Priority Data

Jun. 26, 1986 [FR] France ................... 86 09289

[51] Int. Cl.$^5$ .................. A61K 7/35; A61K 31/74
[52] U.S. Cl. ............................ 424/78; 424/69
[58] Field of Search .............. 424/81, 67, 78, 69; 428/402

[56] References Cited

U.S. PATENT DOCUMENTS 4,089,800 5/1978 Temple ........................... 252/316
4,741,872 5/1988 De Luca et al. ................. 124/486
4,801,445 1/1989 Fukui et al. ..................... 424/78

FOREIGN PATENT DOCUMENTS 61-85309 4/1986 Japan ............................. 424/67

OTHER PUBLICATIONS

Chem. Abstracts, vol. 104:24076w.

*Primary Examiner*—Thurman Page
*Assistant Examiner*—Peter F. Kulkosky
*Attorney, Agent, or Firm*—Cushman, Darby & Cushman

[57] ABSTRACT

A noncompacted powder composition for make-up or for the care of the body and face contains hollow microspheres made of a synthetic thermoplastic material and having a specific mass less than 0.1 g/cm$^3$.

9 Claims, No Drawings

NONCOMPACTED MAKE-UP POWDER OR POWDER FOR THE CARE OF THE BODY AND FACE CONTAINING SYNTHETIC THERMOPLASTIC MATERIAL IN THE FORM OF HOLLOW MICROSPHERES

This application is a continuation-in-part of application Ser. No. 07/066,165 filed June 25, 1987, now abandoned.

The present invention relates to the use of, in the preparation of noncompacted powders for make-up or for the care of the body or face, a synthetic thermoplastic material in the form of hollow microspheres having a low density, as well as to compositions in the form of a noncompacted powder containing such a material.

It is known that certain compositions for make-up or for the care of the skin of the face or body are provided in the form of noncompacted powders, called "free powders". These compositions are principally make-up powders, deodorant powders or even body powders.

Such powder compositions must possess several types of properties.

They must be able to absorb water and, optionally, oily materials which are exuded by the skin. This absorbing power must, however, be limited so as not to give an impression that the skin is drying out. Besides, these compositions must not agglomerate under the effect of ambient humidity.

The powder compositions must be free of any abrasive character, and must possess an unctuous touch or feel.

These compositions must also be able to be easily applied and must adhere sufficiently to the skin.

Moreover, facial make-up powders must have good covering power, i.e. conceal minor skin defects. Their opacity, however, must be limited so as to avoid producing a "floury" appearance on the skin.

Finally, the powders must be compatible with the presence of a certain amount of oil, which improves the comfort of application, and which can serve as a vehicle for various active components (U.V. filters, perfumes, vitamins, softening agents and the like).

There does not exist any known pulverulent material having all these properties which, as can easily be seen from the above discussion, are somewhat contradictory in nature and the difficulties of producing such powders are resolved by producing mixtures of various components which establish an equilibrium among all the desired properties.

It has now been discovered that it is possible to produce fine and light noncompacted powders, that (1) are only slightly sensitive to ambient humidity, (2) have an unctuous feel, (3) are capable of including relatively high amounts of oil without having a tendency to agglomerate, (4) are easy to spread and (5) give the user a sensation of comfort, by incorporating, in the noncompacted powder composition for make-up or for the care of the face or body, a synthetic thermoplastic material provided in the form of hollow microspheres having a very low density.

The preparation of such hollow microspheres is known. The preparation can be carried out, for example, in accordance with the procedures described in U.S. Pat. No. 3,615,972 and European patent application No. 0056219.

The hollow portion of the microspheres contains a gas such as Freon or a hydrocarbon (butane, pentane) or any other generally employed gas.

A significant characteristic of the hollow microspheres which are employed in accordance with the invention is that they have been obtained by a process including a hot expansion stage, for example, in an atomizer, as described in European patent application No. 0056219. This permits the production of hollow microspheres having a very low density, having a specific mass lower than 0.1 g/cm$^3$, and even, preferably, lower than 0.05 g/cm$^3$, so that weight amounts in the order of 3% correspond to volume amounts in the order of 50%. It has been noted that, in a surprising fashion, these microspheres, when they are mixed with more dense particles of other components, provide powders which remain homogeneous, i.e. no segregation of the particles is observed.

The microspheres employed in the noncompacted powder compositions according to the present invention can be produced from any nontoxic and nonirritating thermoplastic material. These materials can be, for example, polymers or copolymers derived from ethylenic hydrocarbons (for example, polyethylene, polystyrene, copolymers of vinyl chloride-acrylonitrile, etc.), polyamides, polyesters, urea-formaldehyde polymers, copolymers of acrylonitrile and vinylidene chloride, etc.

Preferably, the thermoplastic material constituting the hollow microspheres used in accordance with the present invention is a copolymer containing, by weight, 20 to 60 percent of units derived from vinylidene chloride, from 20 to 60 percent of units derived from acrylonitrile, and from 0 to 40 percent by weight of units derived from an acrylic or styrene monomer, the sum of the percentages of the cited components being equal to 100.

The acrylic monomer is, for example, a methyl or ethyl acrylate or methacrylate, and preferably methyl methacrylate. The styrene monomer is, for example, α-methyl styrene or styrene.

Representative hollow microspheres having a low density obtained with these thermoplastic materials, include, in particular, those sold commercially under the trade name "EXPANCEL" by Kemanord Plast AB, Sundsvall (Sweden).

The size of the hollow microspheres usefully employed in the present invention is generally less than 70 μm, and preferably in the order of 20 to 60 μm.

To produce the noncompacted powders of the present invention, the hollow microspheres are employed in amounts ranging from 0.2 to 20 percent and preferably from 0.5 to 5 percent, by weight, relative to the total weight of the composition.

The present invention thus relates to the preparation of a noncompacted powder, for make-up or for the care of the body and face, containing hollow microspheres such as defined above, as well as to powders obtained therewith.

The other components present in the compositions in the form of the noncompacted powder of the present invention are components conventionally employed in the preparation of this type of composition.

Representative ones of these components include, principally:

talc, which is a hydrated magnesium silicate, used in the form of particles generally having a size less than 40 μm; the talc possesses humidity absorbing characteristics and is employed especially because of its unctuous feel;

micas, which are provided in the form of flakes having a diameter preferably less than 70 μm and a thickness less than 5 μm; the micas are aluminosilicates of various compositions, which are provided in the form of flakes having a size ranging from 2 to 200 μm, preferably from 5 to 70 μm and a thickness of 0.1 to 5 μm, preferably from 0.2 to 3 μm. The micas can be of natural origin (for example, muscovite, margarite, roscoelithe, lepidolithe, biotite), or of synthetic origin. The micas are generally transparent and impart to the skin a satiny appearance;

starch, in particular rice starch;

kaolin, which is a hydrated aluminum silicate, which is provided in the form of particles having an isotrope form and having a size generally less than 30 μm; they possess good oily body absorption properties;

oxides of zinc and titanium, generally employed in the form of particles having a size not exceeding a few micrometers (or even less than 1 μm in the case of titanium oxide); these oxides have an unctuous feel, good covering power and a significant opacity;

precipitated calcium carbonate which, in the form of particles having a size less than 10 μm, has an unctuous feel and a nonshiny appearance;

magnesium carbonate or hydrocarbonate which possesses principally perfume fixation properties;

metallic soaps derived from an organic carboxylic acid having 8 to 22 carbon atoms, preferably 12 to 18 carbon atoms, for example zinc, magnesium or lithium stearate, zinc laurate, magnesium myristate, etc. These soaps, provided generally in the form of particles having a size less than 10 μm, have an unctuous feel and facilitate the adherence of the powder to the skin;

powders of synthetic polymers, such as polyethylene, polyesters (for example polyethylene isophthalate or terephthalate), polyamides in the form of particles having a size less than 50 μm, which possess absorbing properties, and impart to the skin a velvety appearance;

natural or synthetic oils, for example, sesame oil, petrolatum oil, liquid lanolin, synthetic triglycerides, macadamia oil, jojoba oil, arara oil (hoplosthetus), and the like. The oils increase the mildness of application, improve the adherence of the powders to the skin and permit the solubilization of certain active components, as indicated above. The powders of the present invention can contain up to 70 weight percent of oil relative to the total weight of the composition, e.g. from 1.5 to 70 weight percent (especially from 1.5 to 50 weight percent). In powders with low oil content, the oil content is most often from 1.5 to 5 weight percent;

the stearate of polyethylene glycol and cetyl alcohol which facilitate the adherence of the powder to the skin;

coloring or nacreous agents, which can be constituted by various colored pigments, metallic powders (for example aluminium or bronze) etc; there can also be employed micas on which has been deposited a layer of pigments or nacreous agents such as for example oxides of titanium, zirconium, iron (III), silica, aluminium hydroxide, bismuth oxychloride, etc; such modified micas are described, for example, in German patent applications 3.211.602 and 3.221.045;

various active components such as antiseptics (trichloro diphenyl ether, cationic agents, boric acid etc.) which are employed principally in body or feet deodorizing powders and in baby powders; astringent agents, which are used in deodorant powders or in foot powders, such as aluminium hydroxychloride or alums, sunscreen agents; softening agents and the like; fillers such as sodium carbonate; and perfumes.

Moreover, the powder compositions of the present invention can be packaged, in combination with a conventional propellant, in a spray container as an aerosol.

It should be understood that all the components which have been listed above are known components used extensively in various types of noncompacted powders for make-up or the care of the body or face. The selection of these components and the determination of the respective amounts make no part of the invention; they are a function principally of supply, economic circumstances, the effect desired, etc. and the criteria of this choice must be considered as being within the skill and knowledge of specialists in this field. What is novel, however, is the combination of one or more of these components with the hollow microspheres defined above.

The present invention thus concerns, principally, a noncompacted powder for make-up or for the care of the body or face containing principally, in addition to the microspheres of synthetic thermoplastic material, oils, polymeric powders, mica, talc, kaolin as well as soaps, pigments and perfumes.

The present invention concerns, in particular, a noncompacted make-up powder having the following composition, by weight:

0.2 to 5 percent of a synthetic material in the form of hollow microspheres, such as defined above;
20 to 94 percent mica,
5 to 45 percent polymeric powder,
0 to 4 percent metallic soap,
1.5 to 5 percent oil,
0 to 30 percent nacreous agent,
0 to 5 percent conventional active component,
and a sufficient amount of perfume and pigments,
the sum of the percentages of the cited components being equal to 100.

The following nonlimiting examples are given to illustrate the present invention.

EXAMPLE 1

A noncompacted make-up powder is prepared having the following composition, weight percent:

| Mica | 55.45 |
|---|---|
| Orgasol 2002 D | 36 |
| Expancel DE | 1 |
| Magnesium myristate | 2 |
| Petrolatum oil | 3 |
| Pigments: | |
| Yellow iron oxide | 1 |
| Black iron oxide | 0.25 |
| DC red 30 | 0.5 |
| Perfume | 0.8 |

The above mica, in powder form, is a product sold, for example by Merck or Mearl.

Orgasol 2002 D is a trade name for a polyamide powder sold by ATO-Chimie.

Expancel DE is a trade name of a composition based on a vinylidene chloride-acrylonitrile type copolymer produced in the form of hollow microspheres having a size ranging from 40–60 μm, containing isobutane, having a specific mass of 0.04 g/cm³ and sold by Kemanord Plast.

This powder is prepared in the following manner:

The mica, Orgasol 2002 D, magnesium myristate and pigments are admixed and then crushed.

The resulting crushed mixture is then pulverized with the perfume to which is then added the petrolatum oil. The Expancel DE is then added by simple mixing.

EXAMPLE 2

In a similar manner a noncompacted make-up powder is prepared having the following weight percent composition:

| | |
|---|---|
| Mica | 46.65 |
| Orgasol 2002 D extra | 28 |
| Expancel DE | 4 |
| Zinc stearate | 5 |
| Arara oil | 5 |
| Nacreous agent | 10 |
| Pigments: | |
| Yellow iron oxide | 0.4 |
| Red iron oxide | 0.3 |
| Black iron oxide | 0.15 |
| Perfume | 0.5 |

This powder is applied very easily to the skin and spreads thereon in a homogenous fashion.

This composition provides a perfect, slightly nacreous, finish to the make-up.

EXAMPLE 3

In a similar fashion a noncompacted make-up powder having the following weight percent composition is prepared:

| | |
|---|---|
| Mica | 70.35 |
| Polymist | 20 |
| Expancel DE | 2 |
| Zinc laurate | 3 |
| Macadamia oil | 1.5 |
| Pigments: | |
| Yellow iron oxide | 1 |
| Red iron oxide | 1 |
| Black iron oxide | 0.15 |
| Perfume | |

Polymist is a trade name for a polyethylene powder sold by Allied Chemical.

This powder is also applied very easily and in a homogenous manner. It leaves a nonshiny finish without any sensation of discomfort.

EXAMPLE 4

Comparative Example

A noncompacted powder (Powder A) having the composition of the powder of Example 1 is produced. However, various pigments have been employed so as to obtain three shades: light, average and deep.

Three other similar powders (Powder B) have been prepared, but without any Expancel DE microspheres.

There was distributed to each of 19 users participating in this test a box of the powder made with Expancel DE (of the desired shade) and a box of the powder of the same shade but without Expancel DE.

The powders were provided in the same type package and were identified only by the letters A or B.

The users have freely tested Powders A and B for 15 days.

The users were then asked to indicate their preference, between powders A and B, on the following criteria: ease of spreading, homogeneity, covering power, nonshiny effect, holding or adherence power and comfort.

The following results were tabulated:

10 users preferred Powder A;

7 users liked both powders;

1 user did not like the powders; and 1 user preferred Powder B.

A statistically significant preference of the users in favor of Powder A has been noted in that which concerns the ease of spreading, the fineness, the softness and comfort. For the other criteria selected, no significant preference was evidenced for Powder A or for Powder B.

EXAMPLE 5

Perfumed Free Powder for the Body

A powder having the following weight percent composition is prepared:

| | |
|---|---|
| Magnesium stearate | 2 |
| Titanium oxide | 4 |
| Kaolin | 4 |
| Expancel DE | 2 |
| Jojoba oil | 2 |
| Superfine talc | 84 |
| Perfume | 2 |

There are introduced into a mixer, magnesium stearate, titanium oxide, kaolin and talc. A pre-mix is effected by stirring. The perfume and jojoba oil are mixed by stirring and the Expancel DE is added until the composition is completely homogenized.

This powder remains homogeneous during storage. It gives to the skin a soft and comfortable feel or touch.

EXAMPLE 6

Baby Talc in the Form of an Aerosol Foam

The following composition (weight percent) has been prepared:

| | |
|---|---|
| Sterile demineralized water | 38.95 |
| Silica | 0.25 |
| Polyethylene glycol stearate | 0.5 |
| Cetyl alcohol | 0.5 |
| Macadamia oil | 1.5 |
| Talc | 20 |
| Perfume | 0.3 |
| Ethanol | 35 |
| Expancel DE | 3 |

Aerosol contents: 90 percent of the above composition and 10% butane (by volume).

The PEG stearate (polyethylene glycol stearate), cetyl alcohol and macadamia oil are mixed together and to the mixture water and alcohol are added.

The talc is then added, as well as the silica and Expancel DE until a homogeneous dispersion is obtained.

The perfume is then introduced into the mixture which is then transferred into an aerosol container which is closed and pressurized.

This talc is easy to use and it produces an agreeable touch on the baby's skin.

EXAMPLE 7

Antiperspirant Powder in Aerosol Form

The following composition (weight percent) has been prepared:

| | |
|---|---|
| Talc | 67.7 |
| Expancel DE | 5 |
| Petrolatum oil | 15 |
| Aluminum hydroxy chloride | 10 |
| Perfume | 2 |
| Colloidal silica | 0.3 |

The propellant consists of a 60–40 mixture (vol/vol) of monochlorodifluoromethane and dichlorofluoromethane.

Aerosol contents: 30% of the above composition and 70% of propellant (by volume).

This antiperspirant produces a sensation of freshness during application, and it retards perspiration without staining clothing.

EXAMPLE 8

Deodorizing Powder for the Body

The following composition (weight percent) has been prepared:

| | |
|---|---|
| Talc | 73.3 |
| Magnesium stearate | 3 |
| Sodium carbonate | 2 |
| Expancel DE | 15 |
| Isopropyl myristate | 5 |
| Trichlorodiphenyl ether | 0.2 |
| Perfume | 1.5 |

This deodorizing powder is agreeable to apply and remains effective all day.

EXAMPLE 9

Deodorizing Powder in Aerosol Form for the Feet

The following composition (weight percent) has been prepared:

| | |
|---|---|
| Talc | 59.2 |
| Magnesium stearate | 5 |
| Expancel DE | 10 |
| Sesame oil | 20 |
| Aluminum hydroxy chloride | 4 |
| Boric acid | 0.5 |
| Perfume | 1 |
| Colloidal silica | 0.3 |

The propellant is identical to that employed in Example 7.

Aerosol contents: 30% of the above composition and 70% of propellant (by volume).

This powder acts efficiently on the degradation of the sweat by bacteria.

EXAMPLE 10

A noncompacted face make-up powder was prepared, having the following composition (weight percent):

| | |
|---|---|
| Mica | 23.42 |
| Kaolin | 0.84 |
| Zinc stearate | 0.84 |
| Yellow iron oxide | 0.12 |
| Brown iron oxide | 0.08 |
| Nylon powder | 14.70 |
| Vaseline oil | 49.20 |
| Perfume | 0.80 |
| Expancel 551 DE | 10.00 |

What is claimed is:

1. A noncompacted powder composition for make-up or care of the body and face having superior oil absorbing effect consisting essentially of hollow microspheres of a vinylidene chloride-acrylonitrile polymer containing by weight 20 to 60 percent of units derived from vinylidene chloride, 20 to 60 percent of units derived from acrylonitrile and 0–40 percent by weight of units derived from an acrylic or styrene monomer and having a specific mass less than 0.1 g/cm$^3$, said microspheres being present in an amount ranging from 0.2 to 20 weight percent based on the total weight of said composition, and an oil present in an amount ranging from 1.5 to 70 weight percent based on the total weight of said composition characterized by base of spreading, fineness, softness and comfort.

2. The noncompacted powder composition of claim 1 wherein said hollow microspheres have a size lower than 70 μm.

3. The noncompacted powder composition of claim 1, wherein said specific mass is less than 0.05 g/cm$^3$.

4. The noncompacted powder composition of claim 1, wherein said amount of oil is from 1.5 to 50 weight percent.

5. The noncompacted powder composition of claim 1 which also contains a powdered polymer, mica, talc, kaolin, a metallic soap, pigment and perfume.

6. A noncompacted make-up powder composition having superior oil absorbing effect consisting essentially of, based on the total weight of said composition, 0.2 to 5 weight percent, as a thermoplastic material, a copolymer of acrylonitrile and vinylidene chloride, in the form of hollow microspheres, 20 to 94 weight percent mica, 5 to 45 weight percent powdered polymer, 0 to 4 weight percent metallic soap, 1.5 to 5 weight percent oil, 0 to 30 weight percent nacreous agent, 0 to 5 weight percent other additives and an effective amount of perfume and pigments, the sum of the percentages of the components being equal to 100 characterized by case of spreading, fineness, softness and comfort.

7. The noncompacted powder composition of claim 1 wherein said acrylic monomer is methyl acrylate, ethyl acrylate, methyl methacrylate or ethyl methacrylate.

8. The noncompacted powder composition of claim 7 wherein said acrylic monomer is methyl methacrylate.

9. The noncompacted powder composition of claim 1 wherein said styrene monomer is styrene per se.

* * * * *